(12) United States Patent
Sirichandra et al.

(10) Patent No.: US 10,646,427 B2
(45) Date of Patent: May 12, 2020

(54) COSMETIC COMPOSITIONS COMPRISING SPICULISPORIC ACID AND AN ESTER OF FATTY ACID AND(POLY)GLYCEROL OPTIONALLY POLYOXYALKYLENATED

(71) Applicant: L'OREAL, Paris (FR)

(72) Inventors: Caroline Sirichandra, Joinville le Pont (FR); Isabelle Terrisse, Vitry sur Seine (FR); Géraldine Lerebour, Les Loges (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/034,418

(22) PCT Filed: Nov. 7, 2014

(86) PCT No.: PCT/EP2014/074102
§ 371 (c)(1),
(2) Date: May 4, 2016

(87) PCT Pub. No.: WO2015/067784
PCT Pub. Date: May 14, 2015

(65) Prior Publication Data
US 2016/0279044 A1    Sep. 29, 2016

(30) Foreign Application Priority Data

Nov. 8, 2013 (FR) .................... 13 60975

(51) Int. Cl.
| | | |
|---|---|---|
| *A61K 31/34* | (2006.01) | |
| *A61K 8/49* | (2006.01) | |
| *A61K 8/37* | (2006.01) | |
| *A61Q 19/00* | (2006.01) | |
| *A61K 8/39* | (2006.01) | |
| *A61K 31/21* | (2006.01) | |

(52) U.S. Cl.
CPC ............ *A61K 8/4973* (2013.01); *A61K 8/375* (2013.01); *A61K 8/39* (2013.01); *A61Q 19/00* (2013.01); *A61K 2800/28* (2013.01)

(58) Field of Classification Search
None
See application file for complete search history.

(56) References Cited

U.S. PATENT DOCUMENTS

| | | | | |
|---|---|---|---|---|
| 2006/0222616 A1* | 10/2006 | Yoneda | ................... | A61K 8/39 424/70.14 |
| 2010/0004472 A1* | 1/2010 | Kitagawa | ............... | A61K 8/602 549/417 |
| 2010/0152139 A1* | 6/2010 | Yoneda | .................. | A61K 8/375 514/99 |

FOREIGN PATENT DOCUMENTS

| | | |
|---|---|---|
| JP | S60 31821 A | 2/1985 |
| KR | 10-2006-0111183 A | 10/2006 |

OTHER PUBLICATIONS

Ishigami et al., "Surface Active Properties of Biosoap from Spiculisporic Acid", Journal of Coltoid and Interface Science, vol. 94, No. 1, Jul. 1983.
M.J. Brown, "Biosurfactants for Cosmetic Applications", International Journal of Cosmetic Science 13, 61-64 (1991).
English Abstract for KR 2006 0111183.
English Abstract for JP S60 31821.

* cited by examiner

*Primary Examiner* — Shobha Kantamneni
(74) *Attorney, Agent, or Firm* — Polsinelli PC

(57) ABSTRACT

This invention concerns a cosmetic composition comprising, in a physiologically acceptable medium, an aqueous phase, spiculisporic acid and/or one of its salts, and at least one ester of fatty acid and optionally polyoxyalkylenated (poly) glycerol.

This invention further concerns the non-therapeutic, cosmetic use of the cosmetic composition as a hygienic product, makeup, a cleaning product, and/or care product of the skin and/or hair.

4 Claims, 1 Drawing Sheet

COSMETIC COMPOSITIONS COMPRISING SPICULISPORIC ACID AND AN ESTER OF FATTY ACID AND(POLY)GLYCEROL OPTIONALLY POLYOXYALKYLENATED

CROSS REFERENCE TO RELATED APPLICATIONS

This application is a National Phase filing under 35 U.S.C. § 371 of PCT/EP2014/074104 filed on Nov. 7, 2014; and this application claims priority to application Ser. No. 1360977 filed in France on Nov. 8, 2013 under 35 U.S.C. § 119. The entire contents of each application are hereby incorporated by reference.

This invention concerns novel cosmetic compositions comprising spiculisporic acid and/or one of its salts, in association with at least one ester of fatty acid and (poly) glycerol, optionally polyoxyalkylenated. The invention further concerns the cosmetic use of the compositions as makeup, a cleaning product, a hygienic product, and/or a skin and/or hair care product.

Desquamation is a natural phenomenon related to the fact that the epidermis, which constitutes the upper layer of the skin and the scalp, is in constant regeneration.

The epidermis consists of several layers of cells, the deepest of which is the basal layer consisting of undifferentiated cells. Over time, these cells differentiate and migrate to the surface of the epidermis, forming the various layers thereof, until, on the surface of the epidermis, they form the corneocytes, i.e., dead cells that are eliminated by desquamation. This loss of surface is compensated by the migration of the cells of the basal layer towards the surface of the epidermis. This means that the skin is in a state of perpetual renewal. Forced elimination of the stratum corneum accelerates renewal and allows aging to be combated.

At the same time, these cells continue differentiating, the last stage of which is the corneocyte. These, in fact, are dead cells constituting the last layer of the epidermis, i.e., the outermost layer, also known as the stratum corneum.

It is known that the desquamation process may be altered by exogenous (e.g., UV radiation, pollution, allergens, pathogens) and/or endogenous (e.g., hormonal changes, age) factors, leading, in particular, to a slowing of the epidermal renewal and, accordingly, aging of the skin, and/or thickening of the stratum corneum (e.g., formation of calluses). Changes in the desquamation process may also result in desquamative disorders both aesthetic (e.g., dandruff, squamae) or pathological (e.g., xeroses, ichthyloses, psoriasis, atopic dermatitis) in nature.

More particularly with regard to skin aging resulting from intrinsic or extrinsic factors, this generally results in a change in the appearance of the skin, which may manifest itself, e.g., as: dry skin, squamae, dull, yellow, or uneven complexion, roughness, and/or cracked skin, wrinkles and small wrinkles, age spots, and/or increased visibility of pores.

There is thus a need to find means of promoting desquamation and/or stimulating the epidermal renewal of the skin.

Thus, this invention concerns a cosmetic composition comprising, in a physiologically acceptable medium, an aqueous phase, spiculisporic acid and/or one of its salts, and at least one ester of fatty acid and optionally polyoxyalkylenated (poly)glycerol.

In fact, the inventors have found, surprisingly, that spiculisporic acid significantly increases the desquamating effect of esters of fatty acid and optionally polyoxyalkylenated (poly)glycerol.

This new combination provides the opportunity to obtain active desquamating bases for care and hygiene for greasy skin, sensitive skin, anti-aging, skin whitening, cleaning, or anti-dandruff.

Spiculisporic Acid

Spiculisporic acid, also known as 4,5-dicarboxy-4-pentadecanolide, has the following formula:

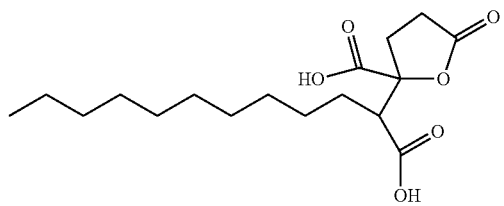 [SMILES: CCCCCCCCCCC(C(=O)O)C1(C(=O)O)CCC(=O)O1]

It is used, in particular, as a surfactant.

According to the invention, spiculisporic acid may be in salt form or not.

According to one embodiment, the spiculisporic acid is in the form of a salt.

Base

The cosmetic compositions according to the invention may also comprise an organic or mineral base.

In the context of the invention, unless otherwise stated, the base used is a neutralising base, i.e., it allows for the neutralisation of spiculisporic acid to form a salt thereof. Examples include sodium, potassium, triethanolamine, and arginine salts of spiculisporic acid.

According to one embodiment, the use of two moles of spiculisporic acid allows for the neutralisation of two carboxylic functions of the acid without breaking the lactone function. In particular, two moles of base are used for one mole of spiculisporic acid in the aforementioned cosmetic compositions.

The base, organic or mineral, may be a Bronsted-Lowry or Lewis base.

Particularly, the base(s) may be selected from:

a) C1-C10 alkanolamines, such as mono-, di-et triethanolamines, isopropanolamine, 2-amino-2-methyl-1-propanol, and derivatives thereof, b) oxyethylenated and/or oxypropylenated ethylenediamines, c) mineral or organic hydroxides, d) alkaline metal silicates such as sodium metasilicates, e) amino acids, preferably basic, such as arginine, lysine, ornithine, citruline, and histidine, f) carbonates and bicarbonates, particularly of a primary, secondary, or tertiary amine, of alkaline or alkaline earth metal, or ammonium, and g) compounds of formula (III) below:

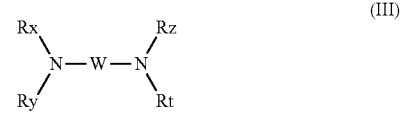

where W is a $C_1$-$C_6$ alkylene residue, which may be substituted by a hydroxyl or $C_1$-$C_6$ alkyl group; Rx, Ry, Rz, and Rt are identical or different, and represent a hydrogen atom, a $C_1$-$C_6$ alkyl group, a $C_1$-$C_6$ hydroxyalkyl group, or a $C_1$-$C_6$ aminoalkyl group.

Examples of such compounds of formula (III) include 1,3-diaminopropane, 1,3-diamino-3-propanol, spermine, or spermidine.

The mineral or organic hydroxides are preferably selected from alkaline metal hydroxides, alkaline earth metal hydroxides, e.g., sodium or potassium hydroxide, transition metal hydroxides, e.g., hydroxides of metals of group III, IV, V, and VI of the periodic table of elements, lanthanide or actinide hydroxides, quaternary ammonium hydroxides, and guanidinium hydroxide.

The hydroxide may be formed in situ, e.g., guanidine hydroxide, which is formed by reacting calcium hydroxide and guanidine carbonate.

According to a particular embodiment of the invention, the base may be selected from the group of inorganic bases, such as sodium hydroxide, potassium hydroxide, lithium hydroxide, cesium hydroxide, calcium hydroxide, magnesium hydroxide, zinc hydroxide, or similar bases, of a basic mineral salt and a basic organic salt containing lithium, sodium, potassium, calcium, magnesium, ammonium, a basic amino acid such as lysine, arginine, histidine, citrulline, ornithine, or the like, a basic oligopeptide having these amino acids as bases, basic amines such as monoethanolamine, diethanolamine, 2-(dimethylamino)ethanol, triethanolamine, triisopropanolamine, diisopropanolamine, monoisopropanolamine, ammonia, or similar bases, other organic bases such as guanidine carbonate, and other similar bases and mixtures thereof.

According to one embodiment in the context of this invention, the base is selected from the group of arginine, triethanolamine, potassium hydroxide, sodium hydroxide, and mixtures thereof.

According to one embodiment, the base is potassium hydroxide.

According to one embodiment, the use of potassium hydroxide allows for the formation of a monopotassium salt, dipotassium salt, or tripotassium salt of spiculisporic acid.

According to the invention, the pH of the composition according to the invention may be between 4 and 10. Preferably, the pH is between 5 and 8, and more preferably between 5 and 6.5.

According to the invention, the spiculisporic acid content may be from 0.1% to 15% by mass relative to the total mass of the composition.

According to a particular embodiment of the invention, the content of spiculisporic acid and/or its salts is between 0.1% and 15%, preferably 0.5% and 10%, more preferably 1% and 8% by mass of the active substance relative to the total mass of the composition.

Compositions according to the invention comprise at least one ester of fatty acid and optionally polyoxy(C4-C36) alkylenated glycerol or optionally polyoxy(C4-C36)alkylenated polyglycerol. The (poly)glycerol esters according to the invention are glycerol (or monoglyceryl) esters or polyglycerol (or polyglyceryl) esters, such as diglyceryl (or diglycerol) esters.

According to one embodiment, the (poly)glycerol ester according to the invention results from the esterification of at least one fatty acid, saturated or unsaturated, and of a (poly)glycerol.

In the context of this invention, the term "(poly)glycerol" refers to glycerol or polymers of glyceryl. In the case of a polymer, polyglycerol is normally a linear chain of 2 to 20, preferably 2 to 10 units of glycerol.

In the context of this invention, the term "polyoxy(C4-C36)alkylenated (poly)glycerol" refers to polyoxy(C4-C36) alkylenated ethers of glycerol (or of polyglycerol) and preferably polyoxyethylenated ethers (or polyethylene glycols) with 1 to 10 repeating units of glycerol or ethyleneglycol.

The esters more specifically contemplated according to the invention are esters resulting from the esterification of (poly)glycerol with 1 to 10 repeating units of glycerol and of $C_4$-$C_{36}$, preferably $C_4$-$C_{18}$, in particular $C_7$-$C_{10}$, carboxylic acid(s).

Generally, they arise from the esterification of at least one hydroxyl function of a (poly)glycerol with 1 to 10 repeating units of glycerol by a $C_4$-$C_{36}$, preferably $C_4$-$C_{18}$, more preferably $C_6$-$C_{12}$, in particular $C_7$-$C_{10}$, carboxylic acid.

According to a particular embodiment, the esters suited for this invention may arise from the esterification of a (poly)glycerol with 1 to 10 repeating units of glycerol by one or more identical or different carboxylic acids. It may be a hydroxylated monoester, a hydroxylated diester, a hydroxylated triester, or mixtures thereof.

A preferred cosmetic composition according to the invention comprises a (poly)glycerol ester selected from the group of glycerol and glycerol polymers.

Fatty Acid

According to one embodiment, the fatty acid is a linear or branched, saturated or unsaturated, carboxylic acid, comprising 4 to 36 carbon atoms, preferably 4 to 18 carbon atoms, more preferably 6 to 12 carbon atoms, in particular 7 to 10 carbon atoms.

Preferably, the fatty acid is a saturated monocarboxylic fatty acid comprising 8 to 18 carbon atoms.

The carboxylic acid may be linear or branched, saturated or unsaturated.

Advantageously, it is a linear monocarboxylic acid.

By way of example only, examples of monocarboxylic acids suitable for the invention include butanoic acid, pentanoic acid, hexanoic acid, heptanoic acid, octanoic acid, nonanoic acid, decanoic acid, undecanoic acid, dodecanoic acid, tridecanoic acid, tetradecanoic acid, heptadecanoic acid, hexadecanoic acid, pentadecanoic acid, and octadecanoic acid (stearic acid).

Representatives of branched acids include, more particularly, isobutanoic acid, isopentanoic acid, pivalic acid, isohexanoic acid, isoheptanoic acid, isooctanoic acid, dimethyloctanoic acid, isononanoic acid, isodecanoic acid, isoundecanoic acid, isododecanoic acid, isotridecanoic acid, isotetradecanoic acid, isopentadecanoic acid, isohexadecanoic acid, 2-ethylhexanoic acid, 2-butyloctanoic acid, and 2-hexyldecanoic acid.

Also suitable for this invention are hydroxy acids such as 2-hydroxybutanoic acid, 2-hydroxypentanoic acid, 2-hydroxyhexanoic acid, 2-hydroxyheptanoic acid, 2-hydroxyoctanoic acid, 2-hydroxynonanoic acid, 2-hydroxydecanoic acid, 2-hydroxyundecanoic acid, 2-hydroxydodecanoic acid, 2-hydroxytridecanoic acid, 2-hydroxytetradecanoic acid, and 2-hydroxyhexadecanoic acid.

More specifically, it is a non-hydroxylated $C_7$-$C_{10}$ acid, more specifically heptanoic acid, caprylic acid, or capric acid.

In the context of this invention, other examples include oxy(C2-C3)alkylenated glycerol esters, in particular polyoxyethylenated esters of glycerol and fatty acid and their hydrogenated derivatives. These oxyalkylenated glycerol esters may be selected, e.g., from the esters of glycerol and of oxyethylenated fatty acid with 4 to 36 carbon atoms, eventually hydrogenated, such as PEG-200 hydrogenated glyceryl palmate, like the one marketed under the name Rewoderm LI-S 80 by Goldschmidt; oxyethylenated glyceryl cocoates such as PEG-7 glyceryl cocoate, like the one marketed under the name Tegosoft GC by Goldschmidt, and PEG-30 glyceryl cocoate, like the one marketed under the name Rewoderm LI-63 by Goldschmidt, and mixtures thereof.

Even more suitable to the invention are the esters selected from mono- and/or di-glyceryl caprylate, mono- and/or di-glyceryl caprate, mono- and/or di-glyceryl heptanoate, mono- and/or di-glyceryl caprylate, propylene glycol caprylate, propylene glycol heptanoate, and mixtures thereof.

More specifically, it is monoglyceryl caprylate (also known as glycerol caprylate), and mixtures thereof.

Examples include the compounds marketed under the name APMUL MCM or AKOLINE MCM (glyceryl caprylate/caprate) by Abitec, DERMOSOFT GMCY (glycerol caprylate) by STRAETMANS, CAPMUL 708 G (GLYCERYL CAPRYLATE and GLYCERYL DICAPRYLATE) by Abitec, as well as CAPMUL 907P (propylene glycol heptanoate) by ABITEC, as well as CAPMUL 908P (propylene glycol caprylate) from ABITEC.

According to one embodiment, the (poly)glycerol ester according to the invention is selected from the group of glyceryl caprylate, polyglyceryl-3 caprylate, polyglyceryl-3 caprate, polyglyceryl-4 caprate, glyceryl laurate, polyglyceryl-2 laurate, polyglyceryl-5 laurate, polyglyceryl-10 laurate, glyceryl myristate, glyceryl stearate, glyceryl undecylenate, glyceryl caprylate/caprate, and mixtures thereof.

In particular, the compounds according to the invention comprise glyceryl caprylate as a (poly)glycerol ester.

The glyceryl caprylate is of use in cosmetics as an anti-microbial agent (acne, deodorant, and dandruff).

According to one embodiment, in the compositions according to the invention, the quantity by mass of ester of fatty acid and (poly)glycerol, which may be polyoxyalkylenated, ranges from 0.1% to 20% relative to the total mass of said composition, preferably 0.5% to 10% and, more preferably 1% to 5%.

Physiologically Acceptable Medium

In addition to the aforementioned compounds, a cosmetic composition according to the invention comprises a physiologically acceptable medium.

In the context of the invention, unless otherwise stated, the term "physiologically acceptable medium" refers to a medium suited to cosmetic applications, suited in particular for the application of a composition according to the invention to the skin and/or hair. The physiologically acceptable medium is generally adapted to the nature of the support on which the composition is to be applied, as well as the appearance to which the composition is to be conditioned.

Aqueous Phase

The composition according to the invention comprises an aqueous phase. This aqueous phase comprises, in particular, water and/or hydrophilic solvents such as polyols.

The water used in the composition according to the invention may be pure, demineralised water, as well as mineral water and/or spring water and/or seawater, i.e., the water of the composition may consist in whole or in part of a water selected from mineral water, spring water, seawater, and mixtures thereof. In general, mineral water is suited for consumption, which is not always the case with spring water. Each of these waters contains, inter alia, solubilised minerals and/or trace elements. These waters are known to be used for the purposes of specific treatments depending on the specific trace elements and minerals they contain, such as hydration and desensitisation of skin or the treatment of certain dermatoses. Mineral or spring water refers not only to natural mineral or spring water, but also natural mineral or spring water enriched with additional mineral and/or trace element ingredients, as well as mineral aqueous solutions and/or aqueous solutions containing trace elements prepared from purified water (demineralised or distilled).

A natural spring water or mineral water used according to the invention may be selected, e.g., from Vittel, Vichy basin, Uriage, Roche Posay, Bourboule, Enghien-les-Bains, Saint Gervais-les-Bains, Néris-les-Bains, Allevar-les-Bains, Digne, Maizières, Neyrac-les-Bains, Lons-le-Saunier, Eaux Bonnes, Rochefort, Saint Christau, Fumades, Tercis-les-bains, Avene water.

The aqueous phase of the composition according to the invention may comprise a water-soluble organic solvent at room temperature (25° C.), selected, e.g., from the lower mono-alcohols including 2 to 6 carbon atoms, in particular 2 to 4 carbon atoms, such as ethanol, isopropanol, propanol, butanol, pentanol, hexanol, polyols with 2 to 20 carbon atoms, preferably 2 to 6 carbon atoms, such as glycerine, propylene glycol, isoprene glycol, butylene glycol, hexylene glycol, polyethylene glycols such as PEG 8, dipropylene glycol, diethylene glycol, and mixtures thereof.

According to a preferred embodiment of the invention, the polyol is glycerine, which provides better comfort during application. Other polyols may be added to the glycerine to the extent that the qualities of the composition are maintained.

The amount of aqueous phase in the composition according to the invention may be 20% to 100% by weight, preferably 40% to 100% by weight relative to the total weight of the composition.

According to a particular embodiment of the invention, the quantity of aqueous phase in the composition is between 95% and 100% by weight relative to the total weight of the composition.

According to one embodiment, the cosmetic compositions according to the invention comprise from 5% to 90% by water mass relative to the total mass of the composition.

The quantity of water in the aqueous phase may be greater than or equal to 10% by weight relative to the total weight of the composition, preferably greater than or equal to 30%, more preferably greater than or equal to 50%.

Preferably, the quantity of water in the composition is between 50% and 95% by weight relative to the total weight of the composition.

The quantity of polyol(s) in the aqueous phase may range, e.g., from 0.5% to 30% by weight, preferably 0.5% to 15% by weight. In particular, this quantity may range from 1% to 10% by weight, preferably 2% to 10% by weight, and more preferably 2% to 8% by weight relative to the total weight of the aqueous phase.

Fatty Phase

The composition according to the invention may compromise a fatty phase.

When present, the fatty phase of the composition according to the invention comprises all fat-soluble or fat-dispersible compositions present in the composition, in particular fats that are liquid at room temperature (25° C.) and atmospheric pressure or oils (which form the oily phase).

The oils present in the composition according to the invention may be silicone or hydrocarbon oil.

Silicone oils refer to oils containing at least one silicon atom, in particular containing Si—O groups.

Examples of silicone oils include volatile silicon oils such as cyclopolydimethylsiloxanes (INCI nomenclature: cyclomethicone), such as cyclopentasiloxane, cyclohexasiloxane, octamethylcyclotetrasiloxane, decamethylcyclopentasiloxane, dodeca-methylcyclohexasiloxane; linear silicones such as heptamethylhexyl-trisiloxane, heptamethyloctyl-trisiloxane, hexamethyl-disiloxane, octamethyl-trisiloxane, decamethyltetrasiloxane, dodecamethyl pentasiloxane; non-volatile silicone oils such as polymethylsiloxanes (PDMS), and phenylated polymethylsiloxanes such as phenyltrimethicones, phenyldimethicones, phenyltrimethylsiloxydiphenyl-siloxanes, diphenyl-dimethicones, diphenylmethyldiphenyl trisiloxanes, 2-phenylethyltrimethyl-siloxysilicates, and polymethylphenylsiloxanes; fatty acid-modified polysiloxanes, fatty alcohols, or polyoxyalkylenes, and mixtures thereof.

The term "volatile" refers to a compound capable of evaporating upon contact with the skin in less than one hour at room temperature and atmospheric pressure. The volatile oil is a volatile cosmetic oil, liquid at room temperature, in particular having a vapour pressure other than null at room temperature and atmospheric pressure, in particular having a vapour pressure from 0.13 Pa to 40 000 Pa ($10^{-3}$ to 300 mmHg), and preferably 1.3 Pa to 13,000 Pa (0.01 to 100 mmHg), and preferably 1.3 Pa to 1300 Pa (0.01 to 10 mmHg).

A hydrocarbon oil refers to an oil essentially formed or consisting of carbon and hydrogen atoms, and possibly oxygen or nitrogen atoms, and not containing an atom of silicon or fluorine; it may contain ester, ether, amine, or amide groups.

Examples of oils that may be used in the composition according to the invention include:

hydrocarbonated vegetable oils such as squalane, liquid triglycerides of fatty acids having 4-30 carbon atoms such as triglycerides of heptanoic or octanoic acid or, e.g., jojoba, babassu, sunflower, olive, coconut, brazil nut, marula, maize, soya, squash, grapeseed, flaxseed, sesame seed, hazelnut, apricot, macadamia nut, arara, coriander, castor, avocado oil, triglycerides of caprylic/capric acid such as those marketed by Stearineries Dubois or those marketed under the names Miglyol 810, 812, and 818 by Dynamit Nobel, shea butter oil;

synthetic esters and ethers, in particular of fatty acids, such as oils having the formulae $R^1COOR^2$ and $R^1OR^2$ wherein $R^1$ represents the residue of a fatty acid or a fatty alcohol having 8 to 29 carbon atoms, and $R^2$ represents a hydrocarbonated chain, branched or not, containing 3 to 30 carbon atoms, e.g., Purcellin oil, octyl-2-dodecyl stearate, octyl-2-dodecyl erucate, isostearyl isostearate; hydroxylated esters such as isostearyl lactate, octylhydroxystearate, octyldodecyl hydroxystearate, diisostearyl malate, triisocetyl citrate, heptanoates, octanoates, decanoates of fatty alcohols; polyol esters such as propylene glycol dioctanoate, neopentylglycol diheptanoate, and diethylene glycol diisononanoate; and pentaerythritol esters such as pentaerythrytyl tetraisostearate;

linear or branched, volatile or non-volatile, hydrocarbons of mineral or synthetic origin, and derivatives thereof, such as branched alkanes having 8 to 18 carbon atoms, e.g. $C_8$-$C_{18}$ iso-alkanes (also known as isoparaffins) such as isododecane, isodecane, isohexadecane, such as the isoparaffins sold under the trade name Isopar by Exxon Chemical or the oils sold under the trade name Permethyl by Presperse, isohexadecaneand isododecane marketed by INEOS; as well as vaseline oil and hydrogenated polyisobutene such as Parléam® oil marketed by Nof Corporation; linear volatile alkanes comprising 7 to 17 carbon atoms such as undecane and tridecane, such as the one described in examples 1 and 2 of patent application WO2008/155059 of Cognis;

fatty alcohols that are liquid at room temperature having 8 to 26 carbon atoms, preferably 12 to 18 carbon atoms, such as octyldodecanol, 2-butyloctanol, 2-hexyldecanol, 2-undecylpentadecanol, or oleyl alcohol; and mixtures thereof Examples include the following oils:

esters arising from the reaction of at least one fatty acid having at least 6 carbon atoms, preferably 6 to 26 carbon atoms, preferably 6 to 20 carbon atoms, more preferably 6 to 16 carbon atoms, and at least one alcohol comprising 1 to 17 carbon atoms, preferably 3 to 15 carbon atoms; examples include, in particular isopropyl myristate, isopropyl palmitate, ethyl-2-hexyl caprate/caprylate (or octyl caprate/caprylate), ethyl-2-hexyl palmitate, isostearyl neopentanoate, isononyl isononanoate, hexyl laurate, lactic acid esters and esters of fatty alcohols comprising 12 or 13 carbon atoms, dicaprylyl carbonate such as that marketed under the name CETIOL CC by COGNIS, fatty acid ethers comprising 6 to 20 carbon atoms such as dicaprylyl ether (such as Cetiol OE from Cognis), glycerol ethers comprising 6 to 12 carbon atoms such as glycerol 2-ethyl hexyl ether (INCI nomenclature: ethylhexylglycerin) such as Sensiva SC 50 from Schulke & Mayr GmbH, octydodecanol, alkanes such as those described in the patent applications of Cognis, WO 2007/068371, or WO2008/155059 (mixtures of distinct alkanes differing with regard to at least one carbon). These alkanes are obtained from fatty alcohols, which, in turn, are obtained from coprah or palm oil.

Examples of linear alkanes suitable for the invention include n-heptane (C7), n-octane (C8), n-nonane (C9), n-decane (C10), n-undecane (C11), n-dodecane (C12), n-tridecane (C13), n-tetradecane (C14), and mixtures thereof. According to a specific embodiment, the volatile linear alkane is selected from n-nonane, n-undecane, n-dodecane, n-tridecane, n-tetradecane, and mixtures thereof.

According to a preferred embodiment, examples of mixtures of n-undecane (C11) and n-tridecane (C13) obtained in examples 1 and 2 of application WO2008/155059 by Cognis;

the polyesters obtained by condensation of dimers and/or trimers of unsaturated fatty acids with 4 to 36 carbon atoms and of diol, e.g., polyesters of dilinoleic acid and diol with 2 to 6 carbon atoms, marketed by Biosynthis under the name Viscoplast, in particular the polymer having the INCI nomenclature dilinoleic acid/propanediol copolymer; and mixtures thereof.

Preferably, the oil is selected from the vegetable oils as listed above.

The amount of fatty phase in the composition according to the invention may be 0% to 80% by weight, preferably 0.1% to 60% by weight relative to the total weight of the composition.

According to a particular embodiment of the invention, the quantity of fatty phase in the composition is between 0% and 5% by weight relative to the total weight of the composition.

Additives

A cosmetic composition according to the invention may also comprise any additive usually used in the field in question, selected, e.g., from gums, resins, dispersants, surfactants, semi-crystalline polymers, antioxidants, essential oils, preservatives, scents, neutralisers, antiseptics, UV protective agents, cosmetic agents such as vitamins, moisturisers, emollients, or collagen protectors, and mixtures thereof.

It is a routine operation for a person skilled in the art to adjust the nature and quantity of the additives present in the compositions according to the invention such that the desired cosmetic properties and stability properties thereof are not affected.

Uses

This invention further concerns the cosmetic non-therapeutic use of a cosmetic compound as defined above as a hygienic product, makeup, a cleaning product, and/or care product of the skin and/or hair.

This invention further concerns a non-therapeutic, cosmetic method for hygiene, makeup, cleaning, and/or care of the skin and/or hair comprising a step of applying to the skin at least one layer of the composition as defined above.

This invention additionally concerns the non-therapeutic cosmetic use of spiculisporic acid and at least one ester of fatty acid and (poly)glycerol, possibly polyoxyalkylenated, in a cosmetic composition comprising a physiologically acceptable medium as an agent to promote the desquamation of the skin and/or scalp.

In particular, the cosmetic composition implemented according to this use is a cosmetic composition as defined above, comprising spiculisporic acid and at least one ester of fatty acid and, possibly polyoxyalkylenated, (poly)glycerol, as defined above.

Within the meaning of the invention, "skin" refers in the broader sense to the skin and semi-mucosa (lips).

The compositions according to the invention are more specifically intended for the cosmetic treatment of aging, greasy, dry, and/or hyperpigmentated skin.

The cosmetic compositions according to the invention may be care, sun protection, cleaning (makeup removal), hygiene, or makeup products of the skin and/or hair.

These compositions are thus intended for application to the skin and/or hair.

According to one embodiment, the compositions according to the invention are in the form of a foundation, a makeup remover, a facial and/or body and/or hair care product, an anti-aging product, a sun block, a product for greasy skin, a whitening product, a moisturiser, a BB cream, a tinted moisturiser or a foundation, a hair conditioner, a facial and/or body cleaner, a shower gel, or a shampoo.

The compositions according to the invention are intended, in particular, for improving at least one of the conditions selected from the following:

improving the radiance and/or evenness of the complexion and/or reducing the appearance of uneven and/or dull complexion;

improving the appearance of the surface, in particular reducing the rough or cracked appearance of the skin and/or improving the grain and/or softness of the skin;

smoothing the microrelief of the skin, in particular smoothing small wrinkles and wrinkles and/or reducing marks from acne or varicella;

reducing signs of aging (e.g., age spots) and/or aesthetic pigmentation disorders such as brownish pigment stains and/or freckles;

reducing skin dryness, in particular the dryness of aging skin;

improving the appearance and/or reducing the visibility of pores and/or improving the unclogging of pores;

promoting the cleaning and elimination of dead cells on the skin surface; and/or combating imperfections of greasy skin, in particular the shiny or glossy appearance of the skin.

The compositions according to the invention may also be used for the preparation of compositions for the treatment of pigmentation disorders such as melasma, post-inflammatory hyperpigmentation, accidental hyperpigmentation, possibly due to light sensitisation or wound cicatrisation.

The invention thus concerns the cosmetic use of a composition containing, in a physiologically acceptable medium, spiculisporic acid and an ester of fatty acid and (poly)glycerol, possibly polyoxylalkylenated, as defined above, to improve the radiance and/or homogeneity of the complexion and/or to reduce the appearance of uneven and/or dull complexion.

It further concerns the cosmetic use of a composition containing, in a physiologically acceptable medium, spiculisporic acid and an ester of fatty acid and (poly)glycerol, possibly polyoxyalkylenated, as defined above, to improve the surface appearance, in particular to reduce the rough or cracked appearance of skin and/or to improve the grain and/or softness of the skin, or the cosmetic use of a composition containing, in a physiologically acceptable medium, spiculisporic acid and an ester of fatty acid and (poly)glycerol, possibly polyoxyalkylenated, as defined above, to smooth skin microrelief, in particular to smooth small wrinkles and wrinkles and/or to reduce the marks of acne or varicella.

The invention additionally concerns the cosmetic use of a composition containing, in a physiologically acceptable medium, spiculisporic acid and a fatty acid and (poly)glycerol ester, possibly polyoxylalkylenated, as defined above, to reduce age spots.

It additionally concerns the cosmetic use of a composition containing, in a physiologically acceptable medium, spiculisporic acid and an ester of fatty acid and (poly)glycerol, possibly polyoxylalkylenated, as defined above, to reduce skin dryness, in particular the dryness of aging skin.

The scope of the invention also includes the cosmetic use of a composition containing, in a physiologically acceptable medium, spiculisporic acid and an ester of fatty acid and (poly)glycerol, possibly polyoxylalkylenated, as defined above, to improve the appearance and/or reduce the visibility of pores and/or improve poor unclogging.

The invention additionally concerns the cosmetic use of a composition containing, in a physiologically acceptable medium, spiculisporic acid and an ester of fatty acid and (poly)glycerol, possibly polyoxylalkylenated, as defined above, to promote the cleaning and elimination of dead cells on the skin surface.

It additionally concerns the cosmetic use of a composition containing, in a physiologically acceptable medium, spiculisporic acid and an ester of fatty acid and (poly)glycerol, possibly polyoxylalkylenated, as defined above, to combat imperfections of greasy skin, in particular the shiny or glossy appearance of the skin.

The cosmetic compositions according to the invention are also used to prevent, mitigate, and/or combat the signs of skin aging, improve the appearance and/or texture of the skin and/or scalp, and, in particular, to reduce dyschromias, reduce irregularities in the surface and microrelief of the skin, promote the elimination of dandruff, improve the hold of makeup, and/or improve the result of skin treatment with colorants in the stratum corneum such as dihydroxyacetone (DHA).

Dyschromia refers to all problems in the distribution of skin pigments, both excessive amounts of such pigments (hyperchromia) or the absence thereof (achromia).

Improvement in the hold of makeup and/or DHA-based skin colouration treatments results from the fact that the skin and/or scalp may be prepared prior to the application of the aforementioned makeup and/or colouration by applying a composition according to the invention, which will promote the result of a simultaneous or subsequent treatment with a makeup or colouring agent.

"Signs of skin aging" refers to all changes in the external appearance of the skin and/or its texture due to chronological or light-induced aging, such as wrinkles, small wrinkles, loose skin, soft skin, thinned skin, lack of elasticity or tone of the skin. Desquamating activity is actively sought chiefly in the field of 'anti-aging' compositions, i.e., those intended to combat the cutaneous signs of aging and/or photoaging. However, the combination used according to this invention may also be applied to combat dyschromia or to reduce irregularities in the skin surface and to improve skin microrelief, in particular the reduction of actinic lentigo, acne or varicella marks, cutaneous pore unclogging, the treatment of dry skin, and greasy skin susceptible to acne.

With regard to greasy skin, it is commonly associated with a lack of desquamation and a thick skin grain.

Additionally, excess sebum may promote unchecked development of saprophytic bacterial flora (in particular *Propionibacterium acnes* and *Pityrosporum ovale*) and cause comedones and/or acne lesions. These acne lesions constitute another cutaneous sign of greasy skin that can be advantageously combated using at least one composition according to this invention. To implement the invention, the composition according to the invention may be applied to any area of the skin or its adnexa, in particular the skin, neckline, hands, or lips in order to reduce visible and/or palpable irregularities in the skin, e.g., to reduce scarring, smooth the surface and/or eliminate dead skin, in particular from the lips.

Additionally, numerous skin pathologies are characterised by the production of a thickened stratum corneum and abnormal desquamation, i.e., hyperkeratosis. It may occur on any area of the skin in widely varied clinical contexts. Its pathophysiological underpinnings and etiology are varied.

Advantageously, the compositions according to the invention allow for promotion of desquamation and/or simulation of epidermal renewal, and thus, more specifically, allow for treatment of skin and/or scalp pathologies related to the production of a thickened stratum corneum and/or related to abnormal desquamation.

Accordingly, according to another aspect, this invention further concerns a dermatological composition comprising spiculisporic acid and at least one ester of fatty acid and (poly)glycerol, possibly polyoxyalkylenated, for its use in the treatment of skin and/or scalp pathologies characterized by the production of a thickened stratum corneum and/or abnormal desquamation. By way of example only, these skin and/or scalp disorders related to deregulation of desquamation include, within the context of this invention, xeroses, acne, hyperkeratoses, psoriasis, atopic dermatitis, and ichthyoses.

Within the scope of the invention, and unless indicated otherwise, this ratio R corresponds to the ratio of the number of moles of base over the number of moles of spiculisporic acid. Therefore this is a molar ratio. Mention may for example be made of a molar ratio R strictly greater than 1, and preferably less than or equal to 2.5, thus, a molar ratio R strictly greater than 1 corresponds to a number of moles of base strictly greater than the number of moles of spiculisporic acid.

Preferably, the ratio R is comprised between 1 and 2.5. In particular, the ratio R is equal to 2.

According to an embodiment, the ratio R is comprised between 1.1 and 2.

Throughout the application, "comprising a" or "including a" means "comprising at least one" or "including at least one", i.e., "comprising one or more" or "including one or more" unless otherwise stated.

Throughout the above description, unless otherwise stated, "between x and y" corresponds to an inclusive range, i.e., the values x and y are included within the range.

The invention will be illustrated in the following non-limiting examples. Unless otherwise stated, percentages are expressed by weight relative to the total weight of the composition.

The compositions are prepared according to the usual methods for formulating cosmetic compositions.

EXAMPLES

Example 1

Evaluation of the Desquamating Effect of the Compositions According to the Invention Test Used The Episkin Peeling test measures the detachment of corneocytes of the reconstructed Episkin J13 skin model. At this stage of maturation, the epidermis has a well differentiated stratum corneum (SC).

The sample is treated for 10 minutes with the control or test solution. The sample is taken and placed on the wall of a tube; its surface is then washed with a swab. The washing solution is filtered to preserve only the detached corneocytes. Their presence is measured by a dosage of proteins with the BCA Kit (PIERCE no. 23225).

The reference molecule is glycolic acid (AG). This is one of the compounds used in peeling at rates of occasionally up to 70%. It is applied for short times on the order of a few minutes and then neutralised.

Figure 1:
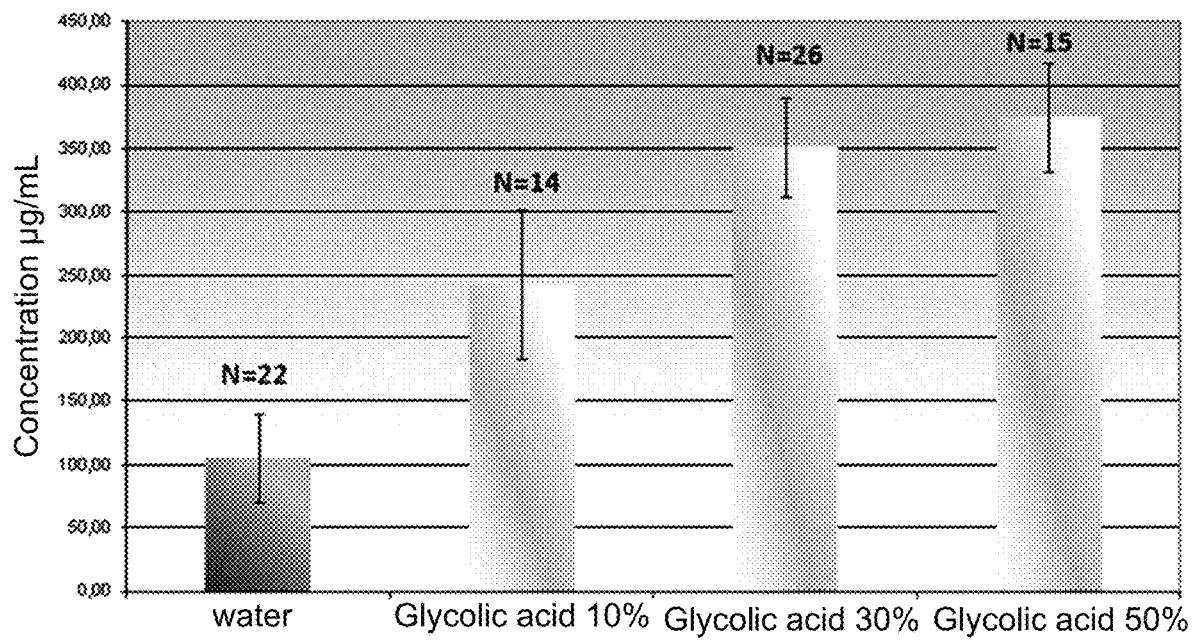
FIG. 1 shows several histograms showing the dose-dependent effect of glycolic acid at 10%, 30%, and 50% on the detachment of corneocytes measured by dosage of proteins.

A dose-dependent effect of AG was obtained over the development of the Episkin Peeling test. The histogram of FIG. 1 shows the responses measured in μg/ml proteins from detached corneocytes. The rate of 30% was used because it allows for good response dynamics with a short application time of 10 min.

Three Episkin batches are used for each study (n=3 per batch and per condition).

The evaluation of the raw materials (MP) is carried out by comparing the results of the MP to those obtained with 30% AG. The MP is effective if it reaches the level of the reference.

Raw Materials Evaluated

The raw materials (MP) and conditions are listed in the table below. They were immersed in water. Spiculisporic acid was salified with potassium (KOH).

| Raw Materials | Rate |
| --- | --- |
| Glyceryl caprylate (Dermosoft GMCY marketed by DR Straetmans) (GMCY) | 5% |
| Citric acid | 10% and 30% |
| Spiculisporic Acid K+ | 1% |
| Spiculisporic Acid K+/GMCY | 1%/5% |
| GMCY/Citric acid | 5%/10% |
| GMCY/Citric acid | 5%/30% |

Results

The desquamating effect was demonstrated by the in vitro peeling test on an Episkin reconstructed skin model as described above with 5% glyceryl caprylate (GMCY) and 1% spiculisporic acid. The dosage of free proteins, measured by DO, is to proportional to the quantity of corneocytes extracted, and thus to desquamation.

Figure 2:
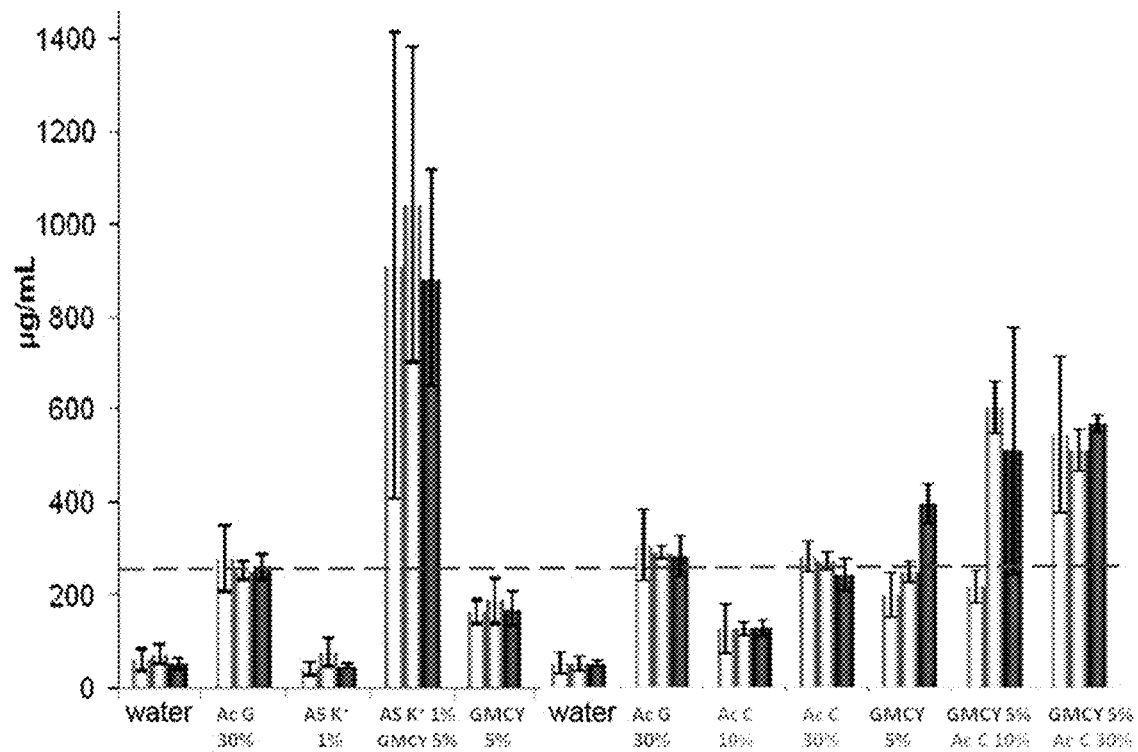
FIG. 2 shows several histograms corresponding to the evaluation of GMCY, citric acid (Ac C), and spiculisporic acid salt (AS K+) alone and in combination on the detachment of corneocytes.

The results are shown by the histograms of FIG. 2.

For MP tested alone, the results obtained show that:

5% GMCY has a desquamating efficacy (almost) reaching that of the glycolic acid reference at 30%.

1% Spiculisporic acid K+ has no effect on the detachment of corneocytes.

10% citric acid does not reach the effect of the reference.

30% citric acid reaches the efficacy level of the reference.

The combination AS K+ 1%/GMCY 5% has an efficacy exceeding that of the glycolic acid reference and exceeds the addition of the effects of the MP alone: There is synergy.

The combination citric acid 10%/GMCY 5% has an efficacy exceeding that of the MP alone.

The combination citric acid 30%/GMCY 5% has an efficacy exceeding that of the MP alone.

Thus, the histograms of FIG. 2 confirm the absence of desquamation with spiculisporic acid alone (AS K 1% column) and positive, but not significant, desquamation relative to the positive control (glycolic acid 30%, Ac G 30% column) for glyceryl caprylate alone (GMCY 5% alone).

On the other hand, the combination of spiculisporic acid and glyceryl caprylate at the same rates (AS K 1%/GMCY 5% column) allows for a significant increase in the desquamating activity well above the positive control. It should be noted that this is not an acid effect because the same combination with citric acid does not provide the same result (columns GMCY 5%/Ac C 10% and 30%).

In conclusion, the combinations tested provide a benefit compared to the effects of the MP used alone at or above the level of that of the reference, glycolic acid.

Example 2

Preparation of Cosmetic Compositions

Example 2.1

Preparation of an Aqueous Solution

| Ingredients | Amounts (% mass) |
| --- | --- |
| Base (KOH or arginine) | qsp pH 6 |
| Water | 94 |
| Glyceryl caprylate (Dermosoft GMCY marketed by DR Straetmans) | 5 |
| Spiculisporic Acid | 1 |

Method of Preparation

Spiculisporic acid is dispersed in water with stirring.

Whilst still stirring, the temperature was increased (40-50° C.) to facilitate the solubilisation of the spiculisporic acid.

The pH was adjusted to 6 using a base (KOH or arginine), and then glyceryl caprylate was added.

The aqueous solution described above was obtained using either potassium or arginine as a base.

Example 2.2

Preparation of an Emulsion

| Ingredients | Amounts (% mass) | Phase |
| --- | --- | --- |
| Spiculisporic Acid | 1 | A1 |
| Water | 67.5 | A1 |
| Base (Arginine) | qsp pH 5 | A1 |
| Glycerine | 5 | A2 |
| Propanediol | 5 | A2 |
| Benzylic acid (preservative) | 0.6 | A2 |
| Xanthan gum (RHODICARE CFT from Rhodia) | 0.1 | A3 |
| Glyceryl caprylate (Dermosoft GMCY marketed by DR Straetmans) | 1 | A4 |
| *Simmondsia chinensis* oil (JOJOBA OIL GOLDEN ORGANIC from Desert Whale) | 6.6 | B |
| Dicaprylic ether | 6.6 | B |
| Undecane (and) tridecane (obtained from examples 1 and 2 of the WO2008/155059 patent application of Cognis) | 6.6 | B |

Method of Preparation

Spiculisporic acid is dispersed in water with stirring.

Whilst still stirring, the temperature was increased (40-50° C.) to facilitate the solubilisation of the spiculisporic acid.

The pH was adjusted to 5 using a base (arginine).

Xanthan gum (A3) was mashed with phase A2, and then glyceryl caprylate to was added.

The mixture was then emulsified at 60° C. by adding phase B to phase A (rotor stator 3000 rpm for 5 min).

The invention claimed is:

1. A cosmetic composition comprising, in a physiologically acceptable medium, an aqueous phase, at least one organic or mineral base, spiculisporic acid and/or one of its salts, and glyceryl caprylate, wherein the spiculisporic acid and/or its salts are present in an amount ranging from 0.1% to 15% by mass relative to the total mass of the composition, and wherein the quantity by mass of glyceryl caprylate ranges from 0.1% to 20% relative to the total mass of the composition.

2. The cosmetic composition according to claim 1, wherein the base is selected from the group consisting of: arginine, triethanolamine, potassium hydroxide, sodium hydroxide, and mixtures thereof.

3. The cosmetic composition according to claim 1, comprising from 5% to 90% by water mass relative to the total mass of the composition.

4. A non-therapeutic cosmetic method for hygiene, makeup, cleaning, and/or care of skin and/or hair comprising a step of applying to the skin at least one layer of the composition according to claim 1.

* * * * *